(12) United States Patent
Salla et al.

(10) Patent No.: US 8,064,979 B2
(45) Date of Patent: Nov. 22, 2011

(54) TEMPERO-SPATIAL PHYSIOLOGICAL SIGNAL DETECTION METHOD AND APPARATUS

(75) Inventors: Prathyusha K. Salla, Waukesha, WI (US); Gopal B. Avinash, New Berlin, WI (US); Cherik Bulkes, Sussex, WI (US)

(73) Assignee: General Electric Company, Schenectady, NY (US)

( * ) Notice: Subject to any disclaimer, the term of this patent is extended or adjusted under 35 U.S.C. 154(b) by 2659 days.

(21) Appl. No.: 10/457,344

(22) Filed: Jun. 9, 2003

(65) Prior Publication Data
US 2004/0249314 A1 Dec. 9, 2004

(51) Int. Cl.
*A61B 5/05* (2006.01)
(52) U.S. Cl. ......... 600/407; 600/410; 600/437; 600/424
(58) Field of Classification Search .................. 600/410, 600/407, 437, 424
See application file for complete search history.

(56) References Cited

U.S. PATENT DOCUMENTS

| | | | | |
|---|---|---|---|---|
| 4,710,717 A * | 12/1987 | Pelc et al. | ...................... | 324/309 |
| 5,195,525 A * | 3/1993 | Pelc | .............. | 600/410 |
| 5,797,849 A * | 8/1998 | Vesely et al. | ................... | 600/461 |
| 5,899,858 A * | 5/1999 | Muthupillai et al. | ......... | 600/410 |
| 5,899,861 A * | 5/1999 | Friemel et al. | ................. | 600/443 |
| 5,987,983 A | 11/1999 | Ariav et al. | ...................... | 73/488 |
| 6,014,473 A * | 1/2000 | Hossack et al. | ................ | 382/294 |
| 6,295,464 B1 * | 9/2001 | Metaxas | ......................... | 600/407 |
| 6,453,187 B1 * | 9/2002 | Prince et al. | ................... | 600/410 |
| 6,501,981 B1 * | 12/2002 | Schweikard et al. | ......... | 600/427 |
| 6,824,516 B2 * | 11/2004 | Batten et al. | .................. | 600/439 |
| 6,892,089 B1 * | 5/2005 | Prince et al. | ................... | 600/410 |
| 6,968,225 B2 * | 11/2005 | Vu | ................. | 600/410 |
| 6,998,841 B1 * | 2/2006 | Tamez-Pena et al. | ......... | 324/302 |
| 7,343,195 B2 * | 3/2008 | Strommer et al. | ............. | 600/424 |
| 2002/0035864 A1 * | 3/2002 | Paltieli et al. | .................. | 73/1.01 |
| 2003/0236466 A1 * | 12/2003 | Tarjan et al. | ................... | 600/508 |
| 2004/0236223 A1 * | 11/2004 | Barnes et al. | .................. | 600/459 |
| 2004/0252870 A1 * | 12/2004 | Reeves et al. | .................. | 382/128 |

OTHER PUBLICATIONS

Three-dimensional left ventricular deformation in hypertrophic cardiomyopathy, AA Young et al. Circulation 1994; 90; 854-867.*
Daniel, F. Leotta et al, Three-Dimensional Ultrasound Imaging Using Multiple Magnetic Tacking Systems and Miniature Magnetic Sensors, 1995, IEEE Ultrasonics Symposium 1415-1418.*

* cited by examiner

*Primary Examiner* — Brian Casler
*Assistant Examiner* — Joel Lamprecht
(74) *Attorney, Agent, or Firm* — Fletcher Yoder

(57) ABSTRACT

A technique for measuring and characterizing the motion of an internal organ is provided. The technique includes using two or more motion-sensitive sensors, disposed on a patient in a region of interest proximate to the internal organ, which acquire motion data along the surface of the patient. The motion data may then be processed and displayed to depict or characterize the mechanical motion undergone by the internal organ. The mechanical motion may be displayed as an image or video. In addition, the mechanical motion data may be combined with other measured data, such as electrical or acoustic data, or with images acquired by other imaging modalities to generate a composite image.

58 Claims, 7 Drawing Sheets

TEMPERO-SPATIAL PHYSIOLOGICAL SIGNAL DETECTION METHOD AND APPARATUS

BACKGROUND OF THE INVENTION

The present technique relates generally to the measurement of mechanical organ motion internal to a subject. More specifically, the present technique relates to measuring internal organ movement via an array of external sensors, such as accelerometers, disposed along the body surface of a subject.

In the medical fields, it is often desirable to measure and characterize the motion of internal organs, such as the heart or lungs, for diagnosis, for processing or interpreting medical imaging data, or for other purposes. In particular, such motion may be indicative of cardiac or respiratory abnormalities that may not be evident from other techniques. Such motion, however, is obviously not directly observable absent an invasive procedure, i.e., surgery, which may be otherwise unnecessary.

As a result, various indicators which can be measured non-invasively may be used as surrogates for the motion of the underlying organ. For example, electrocardiography may be used to measure depolarization of the cardiac muscle tissue, which can then be used to estimate the timing of the contraction phases of the cardiac cycle. In particular, during each phase, different cardiac cells are depolarizing and, presumably, undergoing the subsequent mechanical event of contraction. However, motion aberrations or abnormalities in which the mechanical event of contraction is disassociated from the electrical event of depolarization, due to tissue defect, ionic imbalance, or whatever, may lead to motion defects or abnormalities that are undetected based upon the electrical event depolarization. In such instances, the actual motion of the heart may not be predictable or discernible based on an electrocardiogram, leaving the abnormality undetected and uncorrected.

One alternative is to attempt to measure the underlying motion of the organ of interest using sufficiently sensitive motion sensors, such as, accelerometers, in contact with the surface of the patient. However, because the motion of the organ underlying the surface occurs in three spatial dimensions, a single point measurement from such a sensor is insufficient to accurately represent the full motion of the organ. In particular, a single measurement provides insufficient information to resolve all three spatial dimensions of the internal organ at a moment in time. Therefore, a need exists for a technique allowing the accurate determination of the actual motion of an internal organ in a non-invasive manner.

BRIEF DESCRIPTION OF THE INVENTION

The present technique relates to physiological parameter monitoring and, in particular, to the direct monitoring of the motion of one or more internal organs in a non-invasive manner. In the present technique, two or more motion-sensitive sensors, such as accelerometers, may be affixed upon a patient interface to form a sensor array. The patient interface may then be disposed upon the surface of a subject, such as a patient's skin, near a moving internal organ, such as the heart or lungs. The sensor array then non-invasively acquires mechanical motion data from the sensor array. The temporal data from each sensor may be combined with the spatial data from each sensor to derive the three-dimensional mechanical motion, i.e., movement, of the internal organ. The mechanical motion data may then be used to derive a surface or an internal motion map or for the acquisition and processing of image data via other imaging modalities. In addition, the mechanical motion data may be combined with data from other modalities, such as electrical, acoustic, or image data, to construct maps or images incorporating the different data.

In one embodiment of the present technique, a method is provided for measuring motion associated with one or more internal organs. The method comprises acquiring motion data associated with one or more internal organs undergoing motion from two or more motion-sensitive sensors. The sensors may be disposed on a patient in a region of interest proximate to the one or more internal organs. The motion data comprises a temporal component and one or more spatial components. The motion data is processed to generate a image. The image is displayed via a user interface.

In another embodiment of the present technique, a computer program is provided for measuring motion associated with one or more internal organs. The computer program may be provided on one or more tangible media. The computer program comprises a routine for acquiring motion data associated with one or more internal organs undergoing motion from two or more motion-sensitive sensors. The sensors are disposed on a patient in a region of interest proximate to the one or more internal organs. The motion data comprises a temporal component and one or more spatial components. The computer programs also comprises a routine for processing the motion data to generate a image and a routine for displaying the image via a user interface.

In another embodiment of the present technique, a motion sensing system is provided for measuring motion associated with one or more internal organs. The motion sensing system includes a patient interface comprising two or more motion-sensitive sensors. In addition, the motion sensing system comprises a processor-based system configured to acquire motion data associated with one or more internal organs undergoing motion from the two or more motion-sensitive sensors. The processor-based system is also configured to process the motion data and to display the processed motion data on one or more output devices. The motion sensing system also comprises one or more input devices configured to allow an operator to configure or execute operations on the processor-based system. In addition, the motion sensing system comprises one or more output devices configured to display information provided by the processor-based system.

In a further embodiment of the present technique, a motion sensing system is provided for measuring motion associated with one or more internal organs. The motion sensing system comprises means for acquiring motion data associated with one or more internal organs undergoing motion. The motion sensing system also comprises means for processing the motion data and means for displaying the processed motion data.

BRIEF DESCRIPTION OF THE DRAWINGS

The foregoing and other advantages and features of the invention will become apparent upon reading the following detailed description and upon reference to the drawings in which.

DETAILED DESCRIPTION OF SPECIFIC EMBODIMENTS

In the field of medicine it is often desirable to be able to measure or characterize the mechanical motion of an internal organ or other motion generator. For example, the rhythmic movement of the heart or lungs may be of interest, as might the arrhythmic movement of the stomach and other gastrointestinal organs. These measurements may be used to represent or characterize the motion information, thereby allowing the identification of abnormal or aberrant organ motion. Alternatively, the measurements may be used in conjunction with other with medical imaging technologies, such as positron emission tomography (PET) or computed tomography (CT), to allow more accurate or artifact internal views to be reconstructed of the subject's body. Similarly, the motion data may be combined with the other measurements or data, such as electrical or acoustic measurements or imaging data, to derive composite data sets or maps incorporating the motion data and structural or electrical data.

Figure 1:
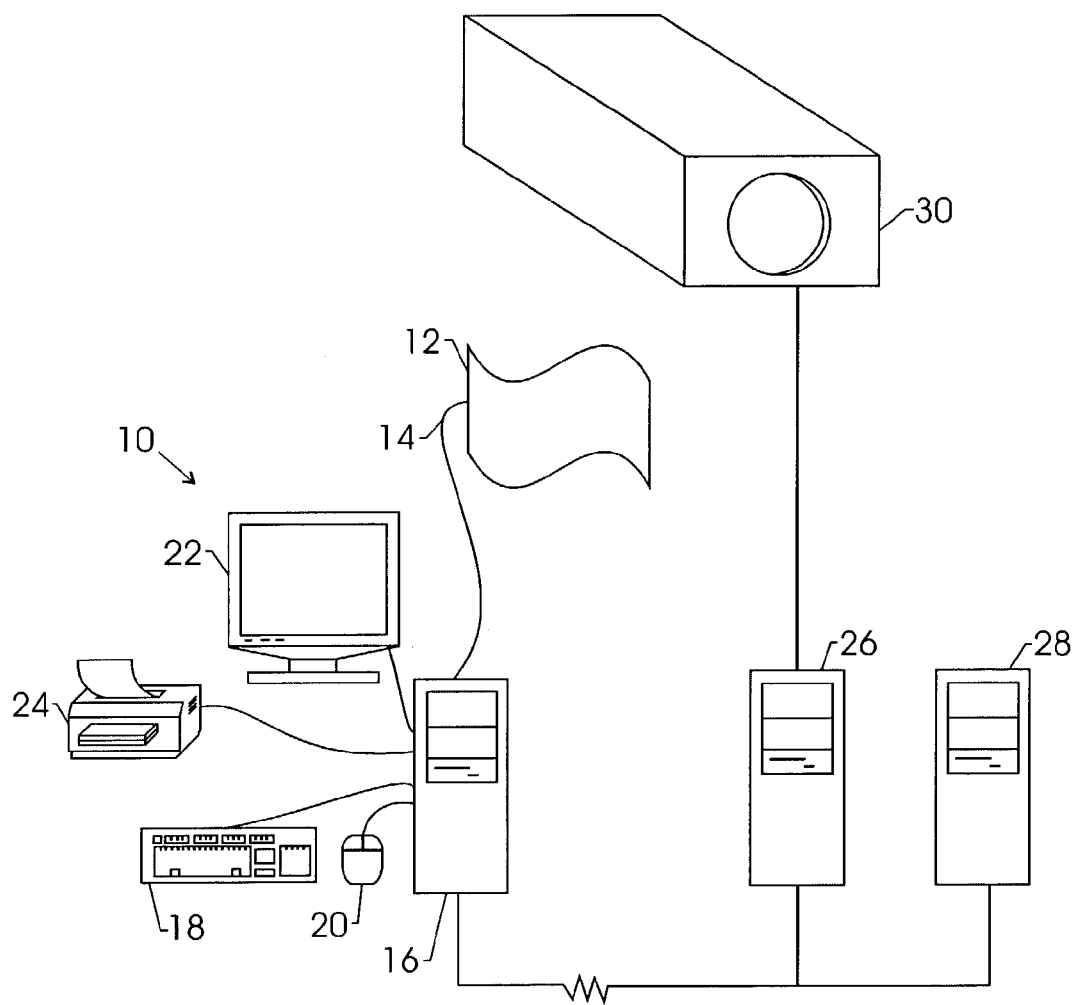
FIG. 1 is a diagrammatical view of an exemplary medical system for use in acquiring motion data of internal organs in accordance with aspects of the present technique.

An example of a system which may be utilized to measure the internal mechanical motion of organs or other internal generators of motion, as opposed to surrogate measures such as electrical activity, is depicted in FIG. 1. The motion sensing system 10 may measure internal motion associated with such organs as the heart, lungs, liver, pancreas, diaphragm, or one or more vascular vessels, such as the peripheral, carotid, aortic, or brachial vessels. The motion sensing system 10 includes a motion-sensitive patient interface 12, such as a pad or sheet, which may be conformed to a portion of the patient's body. The patient interface 12 is connected via one or more leads 14 or other communicative means, including wireless means, to a processor-based system 16, such as a computer or workstation. The processor-based system 16 may include various components in addition to a processor including magnetic and optical mass storage devices, internal memory, such as RAM chips, various input/output (I/O) interfaces, as well as various network or communication interfaces. The various I/O interfaces may allow communication with user interface devices such as a keyboard 18, mouse 20, display 22, and printer 24. The various network and communication interfaces may allow connection to both local and wide are intranets and storage networks as well as the Internet. Remote computers 26, servers, workstations, and archive units 28 may thereby communicate with the processor-based system 16 of the motion sensing system 10. As depicted in FIG. 1, various remote systems such as the remote computer 26, may be in communication with other medical imaging systems, such as a CT system 30. Though the various I/O and communication interfaces are indicated as operating through wires or lines in FIG. 1, it is to be understood that wireless interfaces may also be utilized where appropriate.

As depicted in the exemplary system of FIG. 1, an operator may interact with the processor-based system 16 via various input and output devices, such as the keyboard 18 and mouse 20 as well as the display 22. The operation of the patient interface 12 may thereby be controlled by the operator. Various operational and communication routines or modules, as well as patient and procedure specific information, may be stored locally on the processor-based system 16, remotely on other systems, such as the remote computer 26, or on a readable media, such as an optical or magnetic disk, accessible to the processor-based system 16. The operator may access and execute the stored routines or modules in operating the motion sensing system 10.

The data obtained from the motion sensing system 10 may be used by the operator to generate a motion image or map which may be used in making a diagnosis or planning a treatment. The data obtained may also be used by a separate imaging modality, such as CT system 30, for data acquisition or for image reconstruction. In addition, the data may be combined with other data, such as contemporaneous electrical, acoustic, or imaging data, to generate a composite data representation, such as an image or map, which conveys the motion data in conjunction with the other data. The data may be stored, such as on archive unit 28, for subsequent analysis or processing.

As noted above, the mechanical motion data associated with the internal organ or other motion generator is obtained via the patient interface 12 which is conformed against the skin of a patient. Examples of patient interfaces 12 are depicted on FIGS. 2 and 3. For example, in FIG. 2 the patient interface 12 is depicted as a conformable pad 32 upon which four motion-sensitive sensors 34 are disposed at fixed locations to form a two-dimensional array of sensor elements 34. The sensors 34 may include various types of devices which measure non-electrical events or activity, such as accelerometers, displacement sensors, force sensors, ultrasonic sensors, strain gauges, photodiodes, and pressure sensors. The sensors 34 detect non-electrical events associated with an internal organ or generator which displace the sensors 34 forming the array. For example, internal movement, such as heart beat or respiration, may create mechanical motion detectable by the sensor elements 34 of the array disposed on the skin of the patient. In this manner, internal motion, such as heart valve motion may be detected, measured, and represented, either as a map of surface motion or as a map of internal motion.

The surface area of an individual sensor 34 in contact with the patient may vary from a few $\mu m^2$ to several $cm^2$. In one embodiment, the array may be comprised of two sensors 34. In another embodiment, the array may be formed as a triangle of three sensors 34. However, as many sensors 34 as are desired may comprise the array. The motion-sensitive sensors 34 are highly sensitive to the motion of the patient's skin upon which they are in contact and may return an electrical signal based upon the detected motion of the skin.

Figure 2:
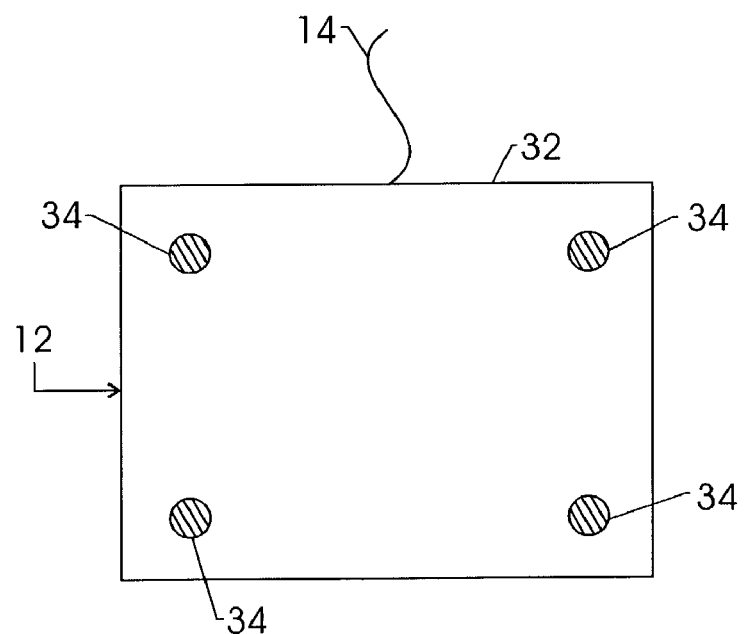
FIG. 2 depicts an implementation of a sensor array for use in conjunction with the system of FIG. 1.
Figure 3:
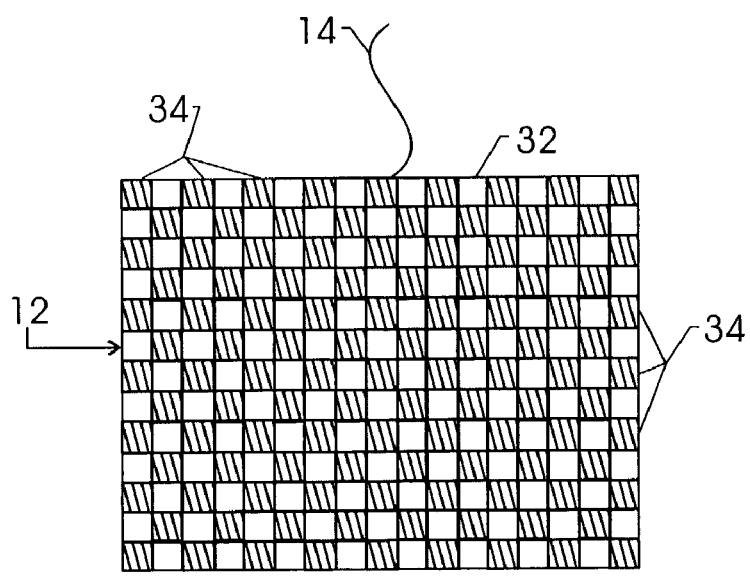
FIG. 3 depicts an alternative implementation of a sensor array for use in conjunction with the system of FIG. 1.

In one embodiment, the array of sensors 34 may be arranged as an N×N grid, up to some desired size of the patient interface 12. In the embodiment depicted in FIG. 3, the array of sensors 34 are equidistant from one another and are arranged as a square grid, i.e., at right angles from one another. Other patterns are possible, however, such as triangular, pentagonal, hexagonal, or octagonal arrangements. Though the arrangements depicted in FIGS. 2 and 3 are two-dimensional for simplicity, configurations of the patient interface 12 are possible in which the sensors 34 are arranged in a three-dimensional matrix such that the entire body surface in the region of interest is covered. For example, the patient interface 12 may comprise a conforming suit or wrap of greater dimensions than the pad 32 depicted in FIGS. 2 and 3. Such a conforming suit or wrap may fully or partially encircle the body surface of the patient in the region of interest, thereby providing mechanical motion data from a greater angular range than may be obtained by a smaller pad 32.

Figure 4:
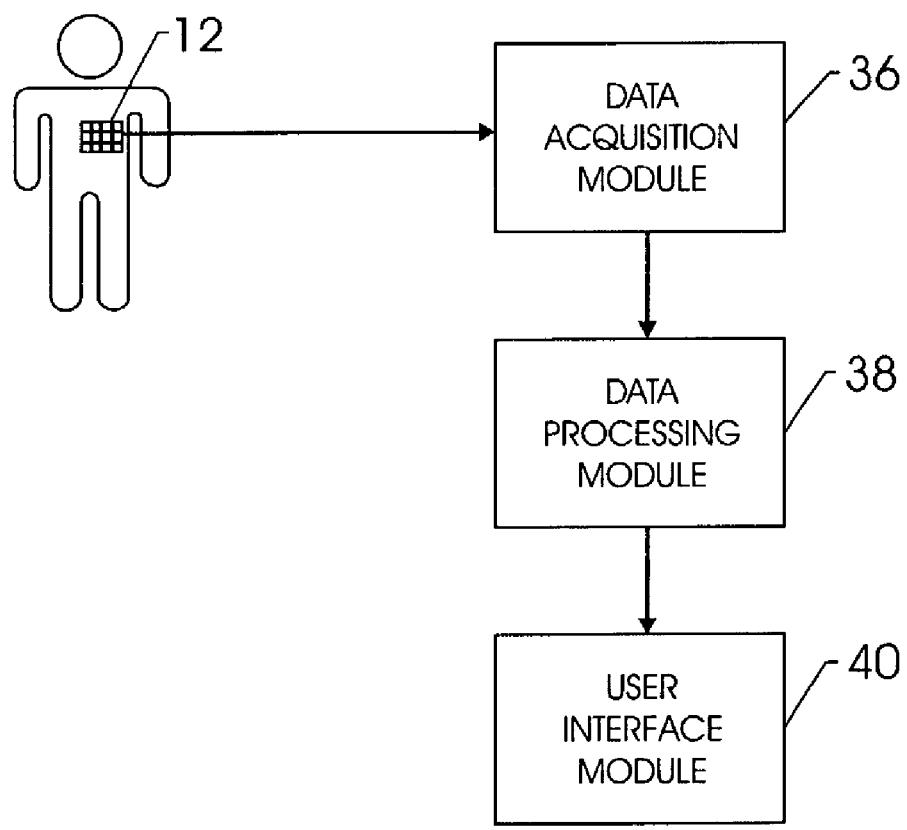
FIG. 4 is a block diagram of various modules which may be used in acquiring motion data of internal organs in accordance with one aspect of the present technique.

Data may be acquired from the patient interface 12 and processed by a variety of modules configured to perform particular steps, as depicted in FIG. 4. The modules discussed below may be executed, separately or together, on the processor-based system 16, upon a system remote from the processor-based, such as remote computer 26, or upon a combination of processor-based platforms. For simplicity, the modules depicted in FIG. 4 are shown as discrete units though, in practice, such modules may comprises a single piece of software or code or may not be designed as discretely separable. To the extent the modules are designed as discrete and separable, however, they may reside on separate pieces of equipment, such as processor-based system 16 and remote computer 26 or upon separate media, such as hard disks, optical disks, or floppy disks.

As depicted in FIG. 4, a data acquisition module 36 may be present to initially acquire raw data from the patient interface 12 disposed on or about the patient to detect mechanical motion on the patient's surface. The data acquisition module 36 may acquire sampled or analog raw data and may perform various operations on the data, such as filtering, multiplexing, and so forth. The sensors 34 allow the acquisition of time information in multiple domains, i.e., a domain for each sensor 34. Comparative or differential surface location data from each sensor 34 may be associated with the respective time data.

A desired operating mode for the data acquisition module 36 may be selected by the operator via the configuration of various acquisition related factors, such as sampling rate, A/D gain, the number of sensor channels, and the selection of two-dimensional or three-dimensional acquisition. The data acquisition module 36 may be programmed to accept a trigger, which may be provided by an operator in one embodiment. A variety of trigger modes may be provided to allow the acquisition module 36 to be conformed to the requirements of the application. Upon receipt of the trigger, the data acquisition module 36 acquires data from the patient interface 12 in accordance with the selected acquisition length and operating mode. Data can be acquired by the acquisition module 36 from all of the sensors 34 on the patient interface 12 or from a subset of sensors 34 within a region of interest.

A processing module 38 may receive the acquired data. Various processing steps may be performed by the processing module 38, including filtering processes or combinations of filtering processes, such as spatial domain filtering (smoothing or sharpening) and frequency domain filtering (frequency filtration and transformations). In addition, point process operations (such as exponentiation), differentiation operations, data segmentation operations (such as discontinuity detection), and thresholding operations (such as global, optimal, or parameter based thresholding), may also be performed by the processing module 38. The processing module 38 may also mark the data with annotations, with delimiting or labeling axes or arrows, or with other indicia for use or display by other modules, such as the user interface module 40. In addition, the processing module 38 may select or eliminate data from specific sensors 34 in the region of interest if this function was not performed by the data acquisition module 36.

Figure 5:
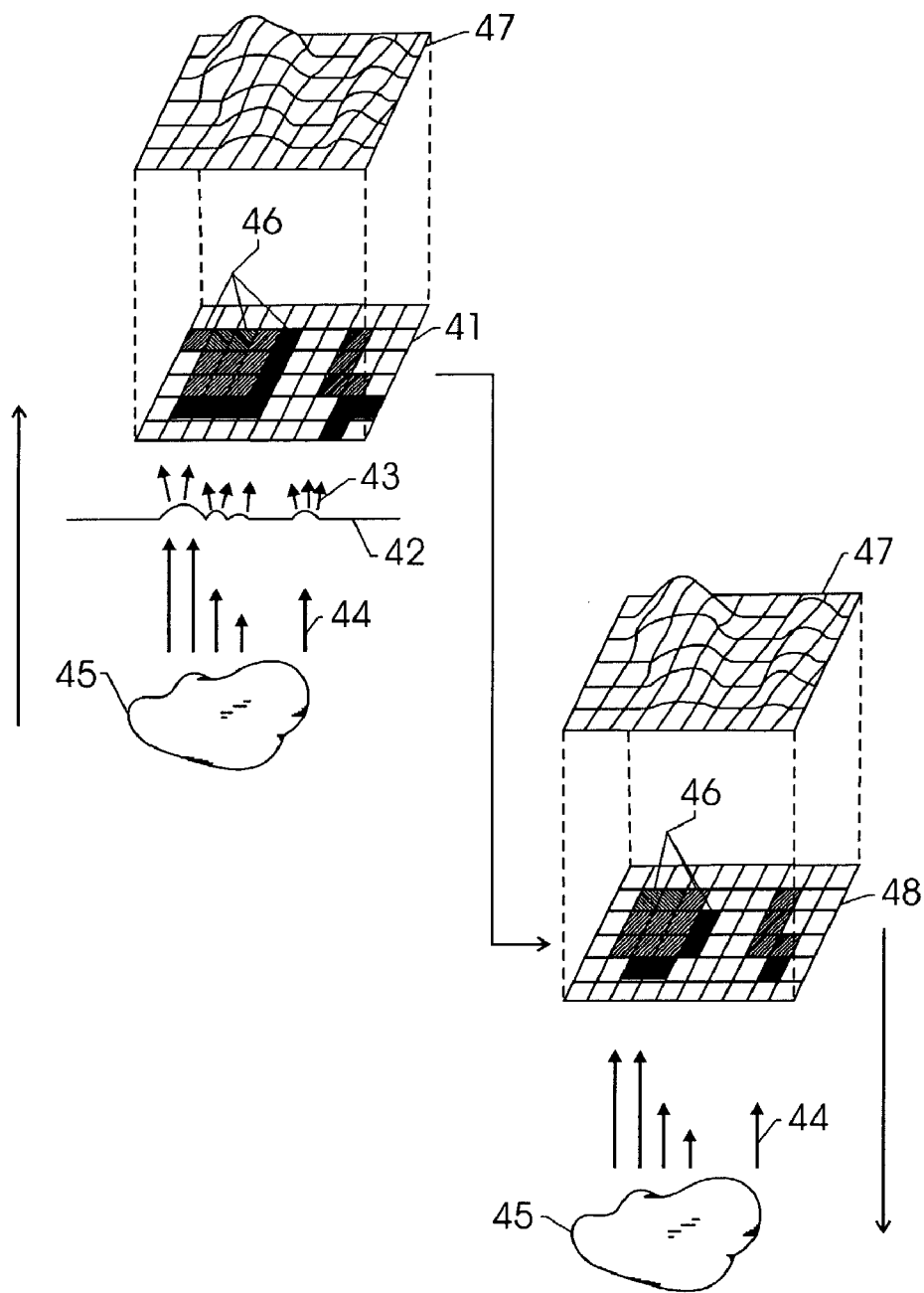
FIG. 5 depicts exemplary surface and internal motion maps generated in accordance with one embodiment of the present technique.

Referring to FIG. 5, the processing module 38 may also derive a surface motion map 41 of the skin surface 42 based on the association of the spatial information with the temporal data. The surface motion map 41 conveys the mechanical motion 43 of the skin 42, as detected by an overlying interface 12, in response to the underlying motion 44 of one or more internal organs 45. The surface motion map 41 may be an image in which the differential displacement or mechanical motion 43 of the skin surface 42 is conveyed by differential color or shading 46.

In the depicted embodiment, the motion map 41 or plot comprises a two-dimensional image corresponding to the motion 43 of the skin surface 42 upon which the sensor array is disposed, at a particular time, t, and location, z. However, other types of representations may be generated from the data, either alone or in combination with other physiological data as described herein, including contour maps 47, bullseye plots, three-dimensional tomograms or renderings, and other derivatives of surface maps such as laplacian and spline maps. Furthermore, parameters derived from the measured motion, such as displacement, velocity, acceleration, and so forth, may also be displayed, alone or in combination with the motion data. The motion or derived data may also be combined with additional physiological data to form composite maps or images. An image, as discussed herein, may be a tomogram, a waveform, or two-dimensional or three-dimensional map or rendering. An image may also comprise a motion film or video, such as a series of renderings, based on all or part of the temporal and spatial data acquired.

In one embodiment, the data comprising the surface motion map 41 may be used to derive a map of the internal motion 44 of the organ 45, as opposed to the surface motion 43 of the skin 42. The resulting internal motion map 48 may be represented in the manners discussed above with regard to the surface motion map 41, including as derived parameters or in combination with other physiological data, such as electrical or structural data. The internal motion map 48 depicts the internal motion 44 of the underlying organ 45 of interest, not the skin surface 42, and may be derived by various techniques, including the use of a transfer function, such as a transfer function associated with an inverse solution set, as discussed herein.

An overview of the flow of information may therefore be observed in the embodiment depicted in FIG. 5. The surface motion 43 of the skin in response to the internal motion 44 of an internal organ 45 may be measured and displayed as a surface motion map 41 in one form or another. The surface motion map 41 may be of interest in itself, but the surface motion data may also be further processed to provide an internal motion map 48, which describes the internal mechanical motion 44 undergone by the internal organ 45. This internal motion 44 may, in turn be displayed in one form or another, as discussed herein.

For simplicity, the depicted motion maps 41, 48, are illustrated at a single time, t, and spatial plane, z. It should, however, be understood that the motion data acquired may comprise multiple times, t, and locations, z. The display of the motion data, therefore, may incorporate more times and locations than depicted in FIG. 5. For example, the motion data may be presented as a tomogram or as a set of maps or plots encompassing multiple t's and z's. Alternately, motion data from the multiple z locations at one time, t, or from multiple times at one location, z may be condensed into a single map or plot. The motion data may also be presented as a video or motion tomogram spanning the times, t, and the measured locations, z.

Figure 6:
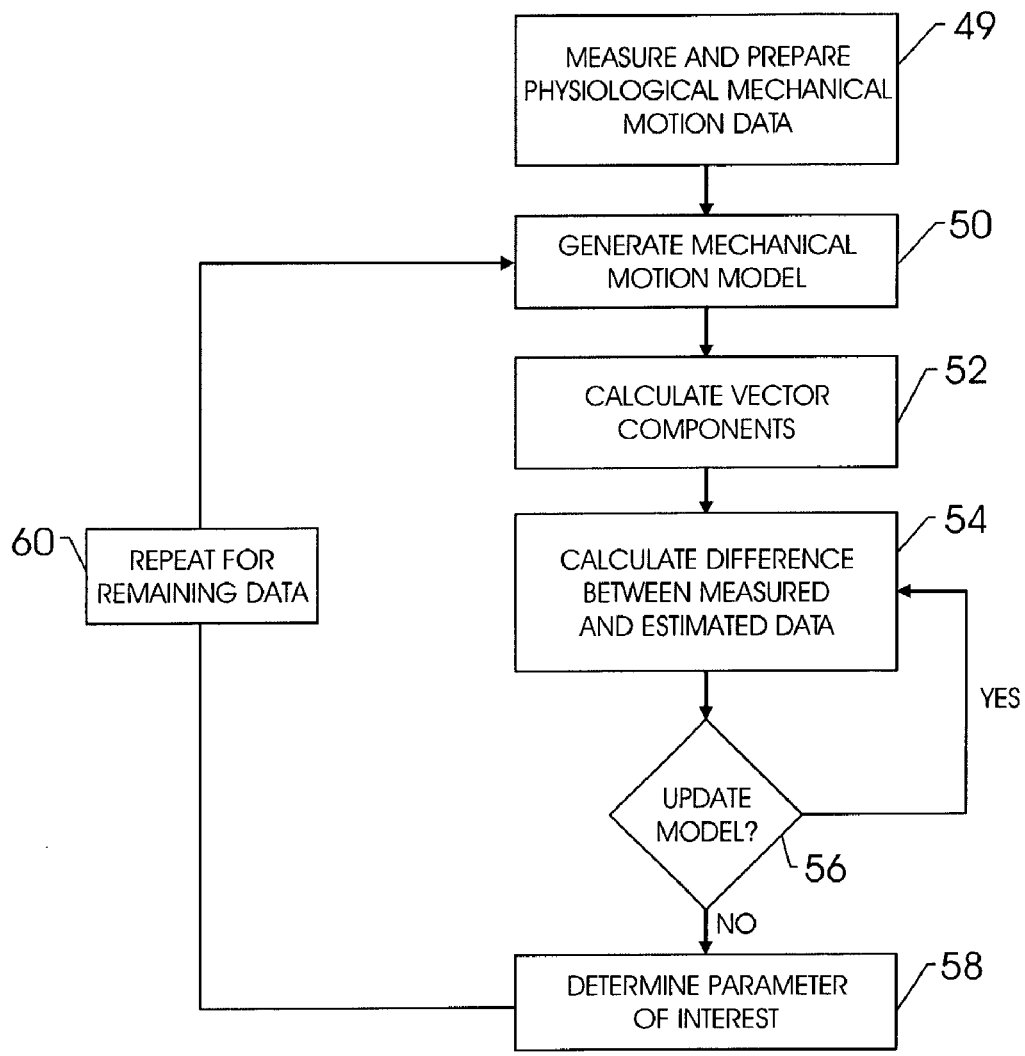
FIG. 6 is a flow chart depicting a process for estimating a parameter of interest from motion data in accordance with the present technique.

As noted above, the internal motion 44 of an organ 45 or other internal generator of mechanical motion may be derived from the measured surface motion data 43. For example, in one embodiment, tensor analysis, particularly solving for the inverse solution set, may be used to derive the internal motion map 48 or image based upon the temporally associated surface motion data 43. In this embodiment, a transfer function may be initially estimated using the acquired data as well as a known signal of greater amplitude to provide scale. The transfer function data along with the acquired temporal and motion data may be input into an inversion process, as depicted at step 49 in FIG. 6. This data may be used to generate a mechanical motion model of the internal region of interest, as depicted at step 50. A value of one or more components of the vector or tensor data at the sensor 34 locations is estimated or calculated for the model at step 52. The difference between the measured data and the estimated data at the sensor 34 locations is then calculated at step 54. A determination may be made at decision block 56 whether or not to update the model, such as if the calculated difference exceeds a configured threshold. If the model is updated, the difference is recalculated at step 54, and so forth, until the difference is minimized or a configured difference threshold is not exceeded. The model is then used to determine the parameter of interest, such as localizing mechanical motion within an interior region of a patient, as depicted at step 58. The modeling process may be repeated, as depicted at step 60, for every instant over time for which data is collected to estimate the parameter of interest over time, such as to localize internal motion over time. The resulting data may be used to generate an image data set, such as the internal motion map 48, a three-dimensional tomogram, or a video, depicting mechanical motion where relative motion is differentiated via color or shading 46. As discussed with regard to FIG. 5, the internal motion map 48 may be of various types and may incorporate or display various parameters derived from the measured motion.

In addition, either the surface map 41 or internal motion map 48 described above may be combined together or with other physiological or image data to form composite images. For example, a composite of the surface map 41 and internal motion map 48 may be generated, using differential shading or color, which differentially depicts relative surface motion in view of the underlying internal motion. Such a composite might be used to facilitate determination of internal motion from the surface motion in other patients.

Similarly, the surface map 41 or the internal map 48 may be combined, separately or together, with other physiological data, such as electrical or structural data, to generate composite images. For example, by combining electrical data, such as an ECG, with the internal motion map 48, one may be able to directly compare the mechanical motion of the heart with the concurrent depolarization events. In this manner, medical personnel may diagnose electrical and mechanical cardiac abnormalities. Similarly, medical personnel may view an internal motion video of the heart while listening to concurrently obtained acoustic data, thereby allowing a trained to clinician to visualize a heart valve problem while listening to the associated murmur.

Figure 7:
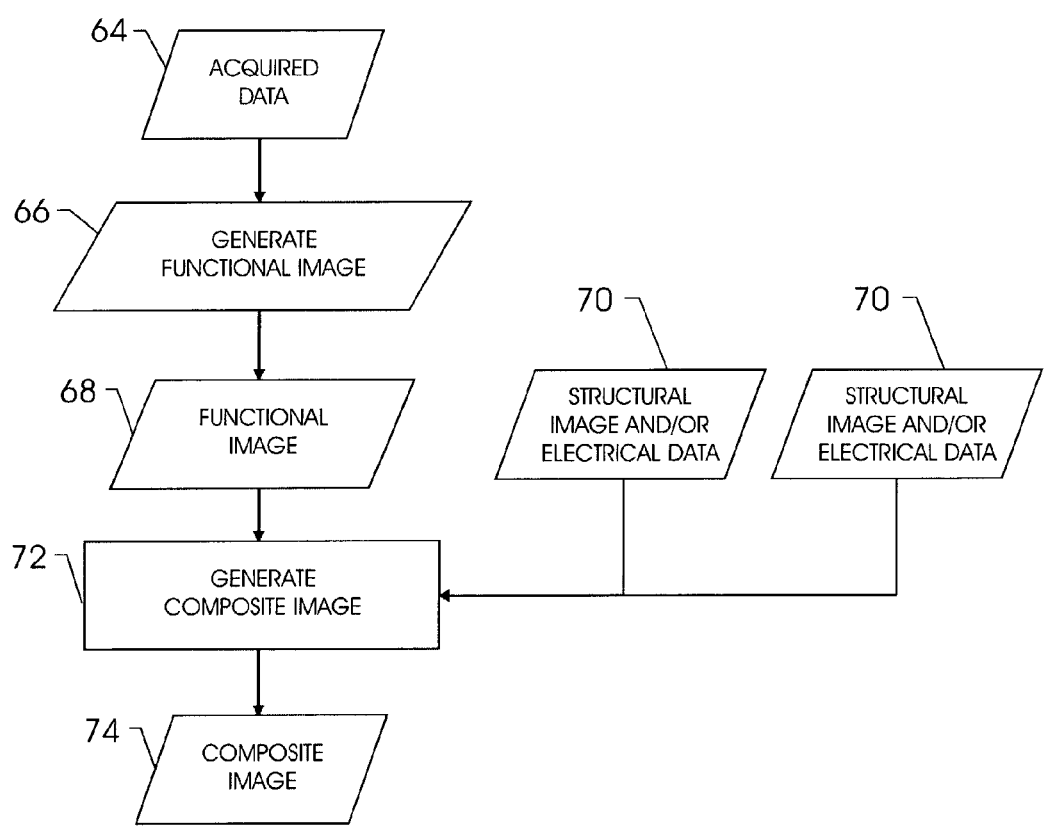
FIG. 7 is a flow chart depicting a process for combining an image acquired via the present technique and another image acquired by an alternate imaging modality.

By combining the functional, i.e., motion, data with other physiological data in this way, greater extended information may be presented to the medical personnel. for example, the surface map 41 or internal motion map 48 may be combined with an anatomical image acquired via a different imaging modality, such as computed tomosynthesis (CT), digital X-ray, magnetic resonance imaging (MRI), positron, emission tomography (PET), and so forth. For example, referring to FIG. 7, the acquired data 64 may be inverse processed at step 66 to generate a motion, i.e., functional, image 68. One or more concurrent or synchronized structural and/or electrical data sets 70 of the region of interest may be combined with the functional image 68 at step 72. The result of the combination is a composite image 74 in which an anatomic and/or electrical framework is integrated with the functional image 68.

In the combining step 72, the appropriate information is extracted from the provided images 68, 70 and combined to form a single composite image 74 with extended information content and detail. In one embodiment, the combining step 72 includes registering, such as by warping, the images 68, 70 to a common reference. The images 68, 70 may also be segmented into constituent components. An analysis may be performed based upon one or more configured criteria to determine the salient portions to be used from each image 68, 70. The composite image 74 is generated by combining the appropriate portions of each image 68, 70.

The user interface or display module 40 may receive the processed data, such as a motion image 41, 48, or a composite image 74, for presentation to an operator. The user interface module 40 allows the processed data to be manipulated, viewed, or output in a user-desired format, such as upon the display 22 or the printer 24. Depending on the type of data acquired, i.e., two-dimensional, three-dimensional, video, appropriate images may be displayed. Color, gray-scale or other coding may be utilized to differentiate the data.

While the above described modules are sufficient to acquire, process, and display data pertaining to internal mechanical motion from an array of sensors 34, additional modules, alone or in combination, may provide added functionality to the process. For example, referring to FIG. 8, a channel selection module 80 may be provided to allow selection of a single channel or multi-channel configuration based upon the application. The channel selection provided by the operator or application may then be used to properly configure data acquisition by the acquisition module 36 and subsequent processing of the acquired data.

Similarly, a calibration module 82 may be used to calibrate the channels associated with the sensors 34 using a known input, such as a phantom. The response of all the sensors 34 to the known, common input can be determined and used to correct non-uniformities in sensor response. The calibration module 82, may flag faulty sensors 34 for exclusion by the data acquisition module 36. Alternately, the calibration data may be communicated to a correction module 84 for determination of correction factors to address non-uniformities in sensor response, for each sensor 34 or for select sensors 34, based upon the calibration results. The correction factors may be calculated by interpolation or other methods. Similarly, the correction module 84 may calculate geometry corrections to compensate for the body curvature of the subject using relative and absolute location references to normalize the data from the multiple sensor locations. The various correction factors may be communicated to a data pre-processing module 86, the data processing module 38, or a data analysis module 88, as appropriate.

The data pre-processing module 86 may be provided for pre-processing the acquired data prior to the processing performed by the processing module 38. For example, the pre-processing module 86 may notch filter the acquired data to avoid interference or may perform an analog-to-digital conversion or drift correction on the data. Depending on the application, pre-processing of this sort may help reduce the time or computer resources needed by subsequent processing steps by conditioning or preparing the data. In addition, the activity of the pre-processing module 86 may allow a reduced sampling rate to be employed during data acquisition while still obtaining data of the desired certain quality. In particular, the data conditioning performed by the pre-processing module 86 may allow the use of a simpler data acquisition protocol by the data acquisition module 36.

The data analysis module 88 may be provided to discover, identify, or characterize the patterns which may exist in the processed data which are relevant to the application. the data analysis module 88 may utilize or incorporate data obtained from other sources, such as timing data or electrocardiogram signals. The analysis performed may include extraction of pertinent data from background "noise," rule-based learning and extrapolation to allow generalization of existing analysis rules to different circumstances, and inference or interpolation based upon incomplete data. In particular, the analysis module 88 may perform routines which allow the detection and classification of features of interest. Pattern recognition techniques, such as template matching, neural networks, and structural methods, which use structural relationship and pattern shape information ascertainable from the data may be used to perform feature detection, i.e., the selection of useful candidate features and the exclusion of redundant information or noise. Feature selection algorithms may also be employed to reduce the dimensionality of the data, thereby reducing the computational time and resources which might otherwise be used to analyze or display an unnecessarily large feature set. In particular, a feature set is selected which allows the different features in signal to be optimally discriminated. Optimization of the feature selection may be based upon various distance measures, such as divergence measures, Bhattacharya distance, Mahalanobis distance, and so forth.

The analysis module 88 may also execute one or more classification algorithms to categorize the detected features or segments of the signal using neural network, rule-based, fuzzy logic, or other techniques. The various detection and classification algorithms employed by the analysis module 88 may be trained using samples of both normal and abnormal, i.e., disease state, data such that the relationship between the processed signals and certain normal and abnormal features may be incorporated by the algorithms.

An archive module 90 may also be provided to store the data or the processed motion maps, images, or video either locally, on the processor-based system 16, or remotely, such as on the archive unit 28. The archiving module 90 may allow reformatting or reconstruction of the data, compression of the data, using either loss-less or lossy techniques, decompression of the data, and so forth. Though the archive module 90 depicted in FIG. 9 receives data from the user interface module 40 and the post-processing module 92, it may also receive data from other modules such as the analysis module 88 or the processing module 38

The post-processing module 92 may receive data from various modules, including the processing module 38, the analysis module 88, the user interface module 40, and the archive module 90. The post-processing module 92 may in turn supply data to the user interface module 40 or, as noted above, the archive module 90. The post-processing module 92 may execute routines to increase the information obtained regarding the temporal and spatial changes in the non-electrical events being measured, such as mechanical motion. The data to be post-processed can be three-dimensional data or four-dimensional data which can be processed in the temporal, the spatial or the temporal and spatial domains respectively. Examples of post-processing routines which may be executed by the post-processing module 92 include basic transformations, fast Fourier transforms (FFT) and other separable image transforms, geometric transformations, and Hotelling transforms. Other possible post-processing routines include image enhancement in spatial and frequency domains, color image processing, image restoration, including algebraic approaches, inverse filtering, least mean squares (Wiener) filtering, interactive restoration, restoration in spatial domains, image segmentation, including discontinuity detection, edge linking and boundary detection, thresholding, region-oriented segmentation, motion utilization in segmentation techniques, and representative or descriptive methods of region differentiation. The post-processed data may be displayed or printed via the user interface module 40 or archived by the archive module 90.

Figure 8:
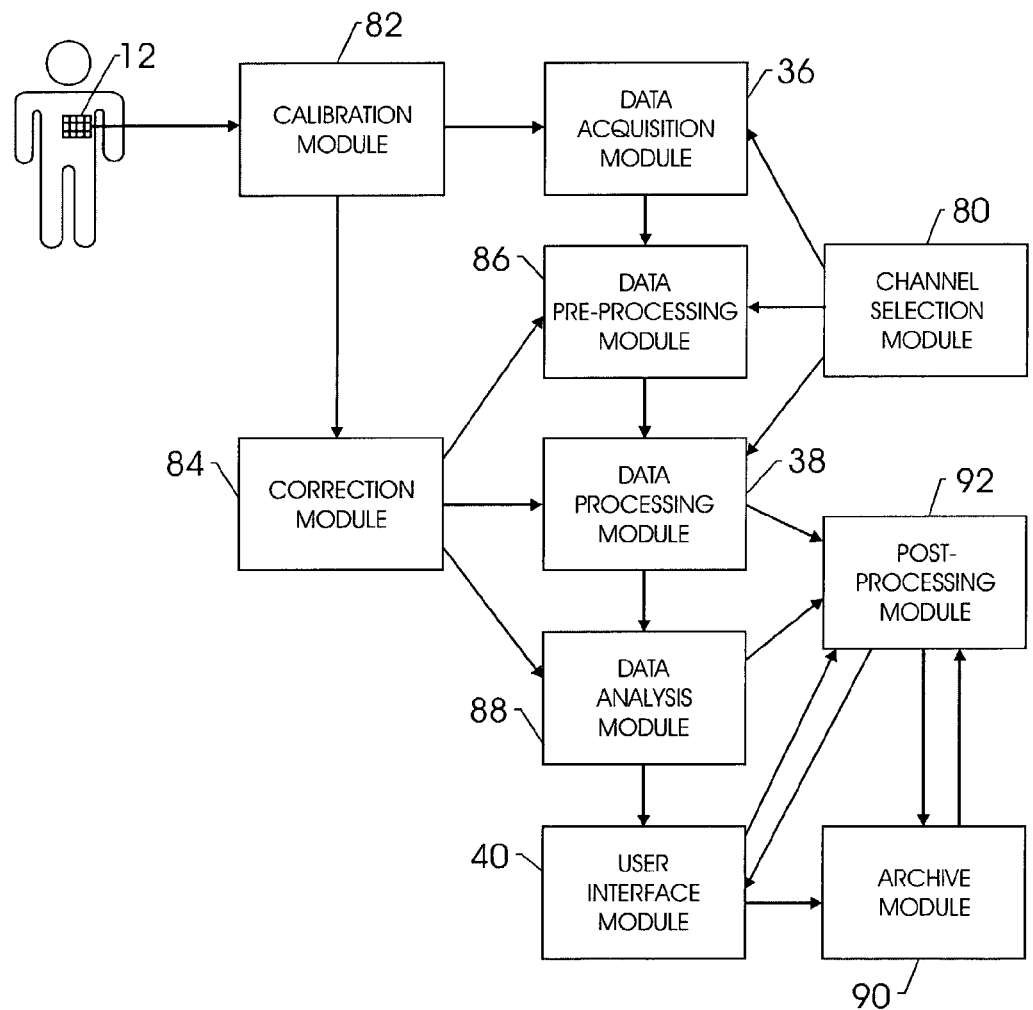
FIG. 8 is a block diagram of various modules which may be used in acquiring motion data of internal organs in accordance with alternative aspects of the present technique.

As noted above, the processed data generated by a system such as that exemplified in FIGS. 4 and 8 may be used to generate color or coded maps or functional images in time and space. The images may be used to analyze the motion or movement on internal generators of mechanical motion, such as the heart or lungs. For example, in the case of the heart, the processed data may allow cardiac activity to be analyzed over multiple cycles, thereby allowing changes in cardiac activity to be viewed from one cycle to the next. The motion data may also be used to generate images of derived parameters which may be of physiological interest or may be combined with other physiological data to generate composite images with extended information.

Other applications of the processed data may include "gating" additional medical imaging modalities, such as CT, PET, MR, PET-CT, digital X-ray, nuclear medicine and ultrasound. Gating techniques facilitate reconstruction of acquired images at the same point in a motion cycle, such as the cardiac cycle, thereby minimizing motion artifacts in the reconstructed images. Alternately, gating techniques may be used to control image acquisition by an alternate modality such that the image data is acquired during a selected phase of internal motion. The accurate detection of internal motion, such as cardiac valve opening and closure, atrial or ventricular contraction and relaxation, and determination of phase in the cardiac or respiratory cycle, may therefore be useful for gating other suitable imaging modalities. In particular, modalities based upon the collection, combination and reconstruction of projections through the body, such CT and PET, may benefit from this data because the timing of the desired phase may be accurately determined, allowing accurate selection of the desired projection data. Accurate selection of the desired projections in turn allows images to be reconstructed with fewer motion artifacts, such as slab shifts, attributable to selection of image data from the wrong phase.

The present technique may also be used for patient monitoring due to the accurate depiction of localized internal motion provided, such as cardiac valve opening and closure. In particular, a database or other storage medium may be used to store data associated with normal and abnormal motion data, such as cardiac motion data, which may be used for comparison of new data. The detected motion map or waveform of a patient may also be displayed for easy visualization and patient monitoring.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A method for measuring motion associated with one or more internal organs, comprising:

acquiring motion data associated with one or more internal organs undergoing motion using two or more motion-sensitive sensors affixed upon a conformable patient interface and disposed on a patient in a region of interest proximate to the one or more internal organs, wherein the motion data comprises a temporal component and one or more spatial components, wherein the conformable patient interface comprises a conformable pad or sheet configured to conform against the skin of the patient;

processing the motion data to generate an image; and displaying the image via a user interface.

2. The method as recited in claim 1, wherein the two or more motion-sensitive sensors affixed to the conformable patient interface remain generally stationary relative to the position of the patient during the acquisition of the motion data.

3. The method as recited in claim 1, wherein the two or more motion-sensitive sensors comprise at least one of accelerometers, displacement sensors, force sensors, ultrasonic sensors, strain gauges, photodiodes, or pressure sensors.

4. The method as recited in claim 1, wherein the region of interest comprises the torso of the patient and the one or more internal organs comprise at least one of the heart, one or more lungs, the liver, the pancreas, the diaphragm, or one or more vascular vessels.

5. The method as recited in claim 4, wherein the one or more vascular vessels comprise at least one of a peripheral vessel, a carotid vessel, an aortic vessel, or a brachial vessel.

6. The method as recited in claim 1, wherein processing the motion data comprises calculating an inverse solution of the motion data such that the image comprises an internal motion image.

7. The method as recited in claim 1, wherein processing the motion data comprises at least one of filtering the motion data, segmenting the motion data, annotating the motion data, or generating subsets of the motion data.

8. The method as recited in claim 1, wherein displaying the image comprises at least one of printing the image on a printer or displaying the image on a monitor.

9. The method as recited in claim 1, wherein the image depicts one of surface motion, internal motion, composite image data, or motion-derived image data.

10. The method as recited in claim 9, wherein the composite image data comprises one of a surface motion image or an internal motion image and one of an electrocardiogram or an anatomical image.

11. The method as recited in claim 10, wherein the anatomical image comprises one of a computed tomogram, a magnetic resonance image, a positron emission tomogram, a CT-PET tomogram, an ultrasound image, or a nuclear medicine image.

12. The method as recited in claim 9, wherein the motion-derived image data comprises at least one of a displacement, a velocity, or an acceleration.

13. The method as recited in claim 1, wherein the image comprises one of a map, a plot, a contour map, a bulls-eye plot, a tomogram, a laplacian map, a spline map, or a video.

14. The method as recited in claim 1, further comprising playing a concurrently obtained physiological acoustic data set in synchrony with the act of displaying the image.

15. The method as recited in claim 1, wherein displaying the image comprises differentially displaying the image using one of color and gray-scale.

16. One or more computer-readable storage media having instructions encoded thereon for measuring motion associated with one or more internal organs, the instructions comprising:

a routine for acquiring motion data associated with one or more internal organs undergoing motion from two or more motion-sensitive sensors disposed on a patient in a region of interest proximate to the one or more internal organs, wherein the two or more motion-sensitive sensors are configured to remain generally stationary relative to the position of the patient during the acquisition of the motion data, and wherein the motion data comprises a temporal component and one or more spatial components;

a routine for processing the motion data to generate a image; and a routine for displaying the image via a user interface.

17. The one or more computer-readable storage media as recited in claim 16, wherein the two or more motion-sensitive sensors comprise at least one of accelerometers, displacement sensors, force sensors, ultrasonic sensors, strain gauges, photodiodes, or pressure sensors.

18. The one or more computer-readable storage media as recited in claim 16, wherein the routine for displaying the image performs at least one of printing the image on a printer or displaying the image on a monitor.

19. The one or more computer-readable storage media as recited in claim 16, further comprising a routine for calibrating the two or more motion-sensitive sensors.

20. The one or more computer-readable storage media as recited in claim 19, further comprising a routine for correcting motion data acquired by the two or more motion-sensitive sensors by one or more correction factors calculated based upon a set of calibration results.

21. The one or more computer-readable storage media as recited in claim 19, further comprising a routine for flagging one or more of the two or more motion-sensitive sensors for exclusion based upon a set of calibration results.

22. The one or more computer-readable storage media as recited in claim 16, further comprising a routine for pre-processing the motion data.

23. The one or more computer-readable storage media as recited in claim 22, wherein the routine for pre-processing performs at least one of notch filtration, analog-to-digital conversion, or drift correction.

24. The one or more computer-readable storage media as recited in claim 22, wherein the routine for acquiring is modified based upon the routine for pre-processing.

25. The one or more computer-readable storage media as recited in claim 16, further comprising a routine for analyzing the motion data.

26. The one or more computer-readable storage media as recited in claim 25, wherein the routine for analyzing performs at least one of pattern recognition, data extrapolation, data generalization, feature detection, or feature classification.

27. The one or more computer-readable storage media as recited in claim 16, further comprising a routine for archiving the motion data.

28. The one or more computer-readable storage media as recited in claim 16, further comprising a routine for post-processing the motion data.

29. The one or more computer-readable storage media as recited in claim 28, where the routine for post-processing performs at least one of fast Fourier transformations, geometric transformations, Hotelling transformations, image restoration, inverse filtering, least mean squares filtering, interactive restoration, image segmentation, discontinuity detection, edge linking, boundary detection, or thresholding.

30. The one or more computer-readable storage media as recited in claim 16, wherein the routine for processing the motion data calculates an inverse solution to the motion data such that the image comprises an internal motion map.

31. The one or more computer-readable storage media as recited in claim 16, wherein the routine for processing the motion data performs at least one of filtering the motion data, segmenting the motion data, annotating the motion data, or generating subsets of the motion data.

32. The one or more computer-readable storage media as recited in claim 16, wherein the image depicts one of surface motion, internal motion, composite image data, or motion-derived image data.

33. The one or more computer-readable storage media as recited in claim 32, wherein the composite image data comprises one of a surface motion image or an internal motion image and one of an electrocardiogram or an anatomical image.

34. The one or more computer-readable storage media as recited in claim 33, wherein the anatomical image comprises one of a computed tomogram, a magnetic resonance image, a positron emission tomogram, a CT-PET tomogram, an ultrasound image, or a nuclear medicine image.

35. The one or more computer-readable storage media as recited in claim 32, wherein the motion-derived image data comprises at least one of a displacement, a velocity, or an acceleration.

36. The one or more computer-readable storage media as recited in claim 16, wherein the image comprises one of a map, a plot, a contour map, a bulls-eye plot, a tomogram, a laplacian map, a spline map, or a video.

37. The one or more computer-readable storage media as recited in claim 16, further comprising a routine for playing a concurrently obtained physiological acoustic data set in synchrony with the act of displaying the image.

38. The one or more computer-readable storage media as recited in claim 16, wherein the routine for displaying the image employs one of color or gray-scale to differentially display the image.

39. A motion sensing system for measuring motion associated with one or more internal organs, comprising:
a patient interface comprising a conformable pad or sheet having two or more motion-sensitive sensors affixed thereon, wherein the conformable pad or sheet is configured to conform against the skin of a patient;
a processor-based system configured to acquire motion data associated with one or more internal organs undergoing motion using the two or more motion-sensitive sensors of the patient interface, to process the motion data, and to display the processed motion data on the one or more output devices;
one or more input devices configured to allow an operator to configure or execute operations on the processor-based system; and
one or more output devices configured to display information provided by the processor-based system.

40. The motion sensing system as recited in claim 39, wherein the one or more input devices comprise at least one of a keyboard or a mouse.

41. The motion sensing system as recited in claim 39, wherein the one or more output devices comprise at least one of a monitor or a printer.

42. The motion sensing system as recited in claim 39, further comprising one or more remote processor-based systems.

43. The motion sensing system as recited in claim 42, wherein the one or more remote processor-based systems include an archive system.

44. The motion sensing system as recited in claim 42, wherein the one or more remote processor-based systems include an imaging workstation and one or more medical imaging systems.

45. The motion sensing system as recited in claim 39, wherein the two or more motion-sensitive sensors comprise at least one of accelerometers, displacement sensors, force sensors, ultrasonic sensors, strain gauges, photodiodes, or pressure sensors.

46. The motion sensing system as recited in claim 39, wherein the processor-based system is configured to process the motion data by calculating an inverse solution of the motion data such that the processed motion data comprises an internal motion map.

47. The motion sensing system as recited in claim 39, wherein the processed motion data depicts one of surface motion, internal motion, composite image data, or motion-derived image data.

48. The motion sensing system as recited in claim 47, wherein the composite image data comprises one of a surface motion image or an internal motion image and one of an electrocardiogram or an anatomical image.

49. The motion sensing system of claim 48, wherein the anatomical image comprises one of a computed tomogram, a magnetic resonance image, a positron emission tomogram, a CT-PET tomogram, an ultrasound image, or a nuclear medicine image.

50. The motion sensing system as recited in claim 47, wherein the motion-derived image data comprises at least one of a displacement, a velocity, or an acceleration.

51. The motion sensing system as recited in claim 39, wherein the processed motion data comprises one of a map, a plot, a contour map, a bulls-eye plot, a tomogram, a laplacian map, a spline map, or a video.

52. The motion sensing system as recited in claim 39, wherein displaying the processed motion data comprises differentially displaying the processed motion data using one of color or gray-scale.

53. The motion sensing system as recited in claim 39, wherein the processor-based system is further configured to play a concurrently obtained physiological acoustic data set in synchrony with the display of the processed motion data.

54. The motion sensing system of claim 39, wherein the conformable pad or sheet is configured to at least partially encircle a body surface of the patient in the general proximity of the region of interest.

55. A motion sensing system for measuring motion associated with one or more internal organs of a subject, comprising:
a patient interface comprising two or more motion-sensitive sensors;
a processor-based system configured to acquire motion data associated with one or more internal organs undergoing motion using the two or more motion-sensitive sensors, to process the motion data, and to display the processed motion data on the one or more output devices, wherein the two or more motion-sensitive sensors are configured to remain generally stationary relative to the position of the subject during the acquisition of the motion data;
one or more input devices configured to allow an operator to configure or execute operations on the processor-based system; and
one or more output devices configured to display information provided by the processor-based system.

56. The motion sensing system as recited in claim 55, further comprising one or more remote processor-based systems.

57. The motion sensing system as recited in claim 56, wherein the one or more remote processor-based systems include an archive system.

58. The motion sensing system as recited in claim 56, wherein the one or more remote processor-based systems include an imaging workstation and one or more medical imaging systems.

* * * * *